US009891218B2

(12) United States Patent
Scott et al.

(10) Patent No.: US 9,891,218 B2
(45) Date of Patent: *Feb. 13, 2018

(54) IMMUNOASSAY PRODUCT AND PROCESS

(71) Applicant: EMD Millipore Corporation, Billerica, MA (US)

(72) Inventors: Chris Scott, Westford, MA (US); Phillip Clark, Wakefield, MA (US); Kurt E. Greenizen, Atkinson, NH (US); Ryan A. Amara, Tewksbury, MA (US); Robert Colonna, Boston, MA (US)

(73) Assignee: EMD Millipore Corporation, Billerica, MA (US)

( * ) Notice: Subject to any disclaimer, the term of this patent is extended or adjusted under 35 U.S.C. 154(b) by 107 days.

This patent is subject to a terminal disclaimer.

(21) Appl. No.: 15/006,153

(22) Filed: Jan. 26, 2016

(65) Prior Publication Data

US 2016/0178625 A1 Jun. 23, 2016

Related U.S. Application Data

(63) Continuation of application No. 13/468,258, filed on May 10, 2012, now Pat. No. 9,272,279.
(Continued)

(51) Int. Cl.
*G01N 21/75* (2006.01)
*G01N 33/558* (2006.01)
(Continued)

(52) U.S. Cl.
CPC .......... *G01N 33/558* (2013.01); *B01L 3/5023* (2013.01); *B01L 9/52* (2013.01);
(Continued)

(58) Field of Classification Search
CPC .......... G01N 33/558; G01N 33/54366; G01N 2469/20; G01N 33/56911; G01N 2469/10;
(Continued)

(56) References Cited

U.S. PATENT DOCUMENTS 4,427,415 A    1/1984   Cleveland
4,717,656 A    1/1988   Swanljung
(Continued)

FOREIGN PATENT DOCUMENTS

CN    1328640 A    12/2001
CN    201382940 Y    1/2010
(Continued)

OTHER PUBLICATIONS

International Search Report and Written Opinion dated Aug. 1, 2012 in corresponding PCT application No. PCT/US2012/037211.
(Continued)

*Primary Examiner* — Dennis White
(74) *Attorney, Agent, or Firm* — Nields, Lemack & Frame, LLC

(57) ABSTRACT

The embodiments disclosed herein are directed to an apparatus useful in conducting detection of compounds on blotting membranes. The device is comprised of several layers including a porous support layer below the blotting membrane(s), a flow distributor above the blotting membrane(s) and optionally a well on the flow distributor to contain the liquid to the desired area and to allow for lower starting volumes of such liquid. Preferably, the flow distributor is a non-binding or low binding hydrophilic porous membrane such as a 0.22 micron membrane and the support layer is a grid or sintered porous material. The distributor and support
(Continued)

are held together to form an envelope around the membrane(s). The use of a hinge, clips and other such devices is preferred in doing so.

13 Claims, 15 Drawing Sheets

Related U.S. Application Data

(60) Provisional application No. 61/484,701, filed on May 11, 2011.

(51) Int. Cl.

| | | |
|---|---|---|
| *G01N 33/543* | (2006.01) | |
| *B01L 3/00* | (2006.01) | |
| *B01L 9/00* | (2006.01) | |
| *G01N 33/569* | (2006.01) | |
| *B01J 20/28* | (2006.01) | |

(52) U.S. Cl.
CPC ..... *G01N 33/54366* (2013.01); *B01J 20/2804* (2013.01); *B01J 20/28033* (2013.01); *B01J 20/28035* (2013.01); *B01L 2200/025* (2013.01); *B01L 2300/069* (2013.01); *B01L 2300/0609* (2013.01); *B01L 2300/0681* (2013.01); *B01L 2300/0809* (2013.01); *B01L 2300/12* (2013.01); *B01L 2300/126* (2013.01); *B01L 2400/049* (2013.01); *B01L 2400/0487* (2013.01); *G01N 33/56911* (2013.01); *G01N 2469/10* (2013.01); *G01N 2469/20* (2013.01)

(58) Field of Classification Search
CPC .... B01L 9/52; B01L 3/5023; B01L 2300/069; B01L 2300/12; B01L 2400/0487; B01L 2300/0609; B01L 2300/0681; B01L 2300/126; B01L 2200/025; B01L 2300/0809; B01L 2400/049; B01J 20/28035; B01J 20/28033; B01J 20/2804
See application file for complete search history.

(56) References Cited

U.S. PATENT DOCUMENTS

| | | | |
|---|---|---|---|
| 4,826,759 A | 5/1989 | Guire et al. | |
| 4,834,946 A | 5/1989 | Levin | |
| 4,948,442 A | 8/1990 | Manns | |
| 5,039,493 A | 8/1991 | Oprandy | |
| 5,108,704 A | 4/1992 | Bowers et al. | |
| 5,141,719 A | 8/1992 | Fernwood et al. | |
| 5,149,408 A | 9/1992 | Perlman | |
| 5,155,049 A | 10/1992 | Kauvar et al. | |
| 5,264,184 A | 11/1993 | Aysta et al. | |
| 5,368,729 A | 11/1994 | Stetkovich et al. | |
| 5,869,272 A | 2/1999 | Bogart et al. | |
| 6,063,579 A | 5/2000 | Bevirt et al. | |
| 6,303,389 B1 | 10/2001 | Levin et al. | |
| 6,395,504 B1 | 5/2002 | Trudil | |
| 6,656,428 B1 | 12/2003 | Clark et al. | |
| 8,460,618 B2 | 6/2013 | Mabuchi et al. | |
| 8,557,600 B2 | 10/2013 | Mabuchi et al. | |
| 8,652,421 B2 | 2/2014 | Mabuchi et al. | |
| 8,652,422 B2 | 2/2014 | Mabuchi et al. | |
| 9,272,279 B2 | 3/2016 | Scott et al. | |
| 2001/0001643 A1 | 5/2001 | Simpson et al. | |
| 2002/0187089 A1 | 12/2002 | Buxbaum | |
| 2003/0143124 A1 | 7/2003 | Roberts et al. | |
| 2004/0048392 A1 | 3/2004 | Kidd | |
| 2004/0171169 A1 | 9/2004 | Kallury et al. | |
| 2004/0245163 A1 | 12/2004 | Lim et al. | |
| 2004/0247490 A1 | 12/2004 | Olivier et al. | |
| 2004/0265186 A1 | 12/2004 | Clark et al. | |
| 2006/0002818 A1 | 1/2006 | Belz et al. | |
| 2006/0078463 A1 | 4/2006 | Shea et al. | |
| 2007/0098601 A1 | 5/2007 | Mabuchi et al. | |
| 2007/0111325 A1 | 5/2007 | Van Beuningen et al. | |
| 2007/0243628 A1 | 10/2007 | Mabuchi et al. | |
| 2011/0038757 A1 | 2/2011 | Mabuchi et al. | |
| 2011/0256025 A1 | 10/2011 | Mabuchi et al. | |
| 2012/0315189 A1 | 12/2012 | Scott et al. | |
| 2014/0011294 A1 | 1/2014 | Mabuchi et al. | |

FOREIGN PATENT DOCUMENTS

| | | |
|---|---|---|
| CN | 201464481 U | 5/2010 |
| CN | 201765230 U | 3/2011 |
| EP | 3312394 A2 | 4/1989 |
| EP | 1151794 B1 | 11/2001 |
| JP | 2-187110 A | 7/1990 |
| JP | 4-227032 A | 8/1992 |
| JP | 2006-17732 A | 1/2006 |
| JP | 2007-163465 A | 6/2007 |
| WO | 92/16294 A1 | 10/1992 |
| WO | 00/20862 A1 | 4/2000 |
| WO | 2004/013607 A2 | 2/2004 |
| WO | 2005/003346 A1 | 1/2005 |

OTHER PUBLICATIONS

International Preliminary Report on Patentability dated Nov. 21, 2013 in corresponding PCT application No. PCT/US2012/037211.
European Search Report dated Feb. 9, 2007 in co-pending European Patent Application No. EP 06255512.3.
European Search Report dated Feb. 9, 2007 in co-pending European Patent Application No. EP 06255513.1.
European Communication dated Apr. 14, 2009 in co-pending European Patent Application No. EP 09153124.4.
Chinese communication, with English translation, dated Aug. 5, 2014 in corresponding Chinese patent application No. CN 201280022626.1.
European communication dated Nov. 24, 2014 in corresponding European patent application No. 14191434.1.
European communication dated Nov. 24, 2014 in corresponding European patent application No. 12781832.6.
Japanese communication, with English translation, dated Sep. 16, 2014 in corresponding Japanese patent application No. 2014-508194.
Biocompare, The Buyers Guide for Life Scientists, Empowering Gene Expression Discoveries, RNA Quality? Unbiased cDNA? qPCR?, "Snap I.D. Protein Detection System From Millipore", dated Monday, Nov. 2, 2009, by Daniel Korostyshevsky, retrieved from the internet, http://www.biocompare.com/Articles/ProductReview/1257/Snap-ID-Protein-Detection-System . . . , Apr. 14, 2011, 2 pages.
Bitesize Bio, "Product Review: Snap i.d. Rapid Western blotting system", dated Oct. 1, 2010 by Emily Crow in Lab Equipment, Protein Biochemistry, retrieved from the internet, http://bitesizebio.com/articles/product-review-snap-i-d-rapid-western-blot-tingsystem/, Jul. 24, 2012, 16 pages.
Office action dated Feb. 23, 2015 in co-pending U.S. Appl. No. 14/022,595.

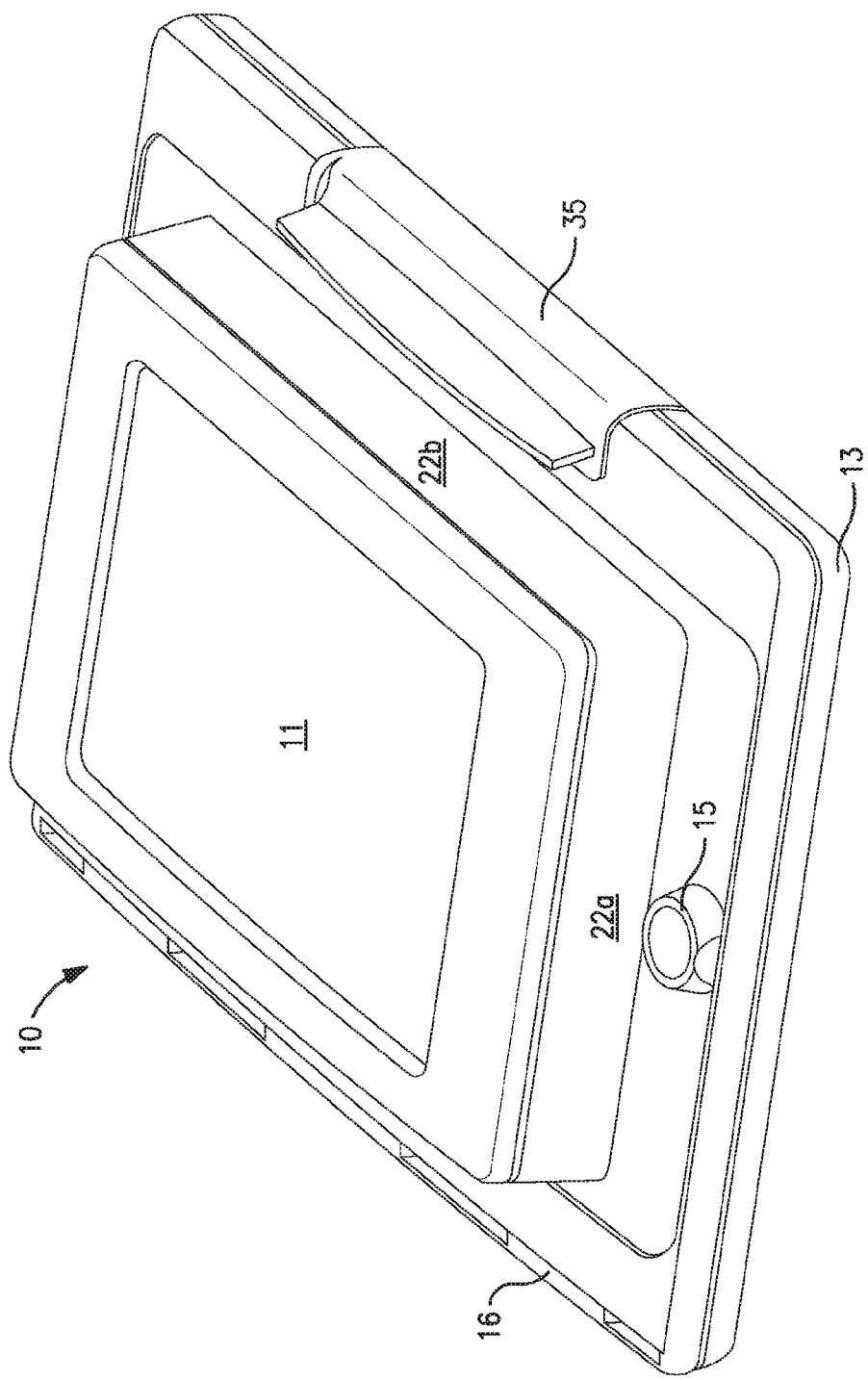

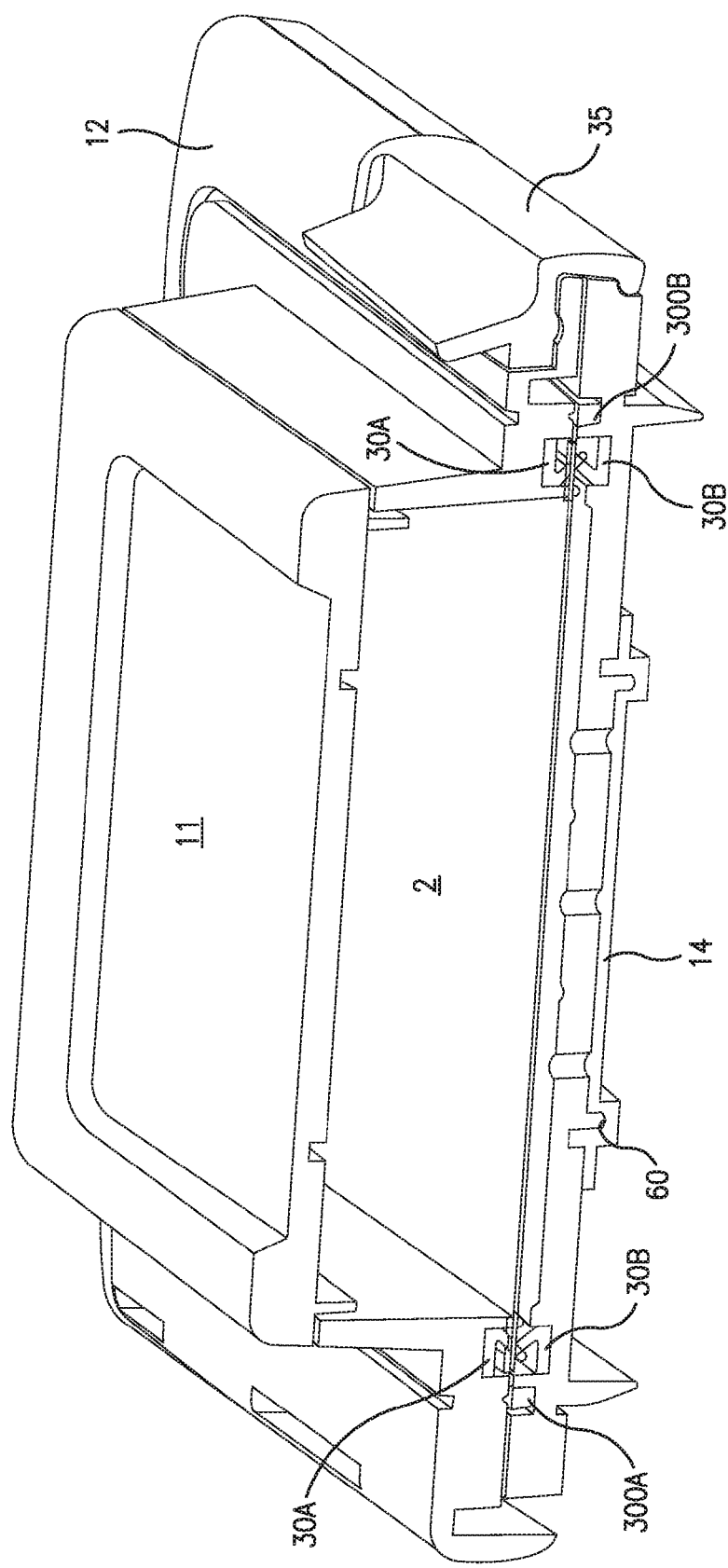

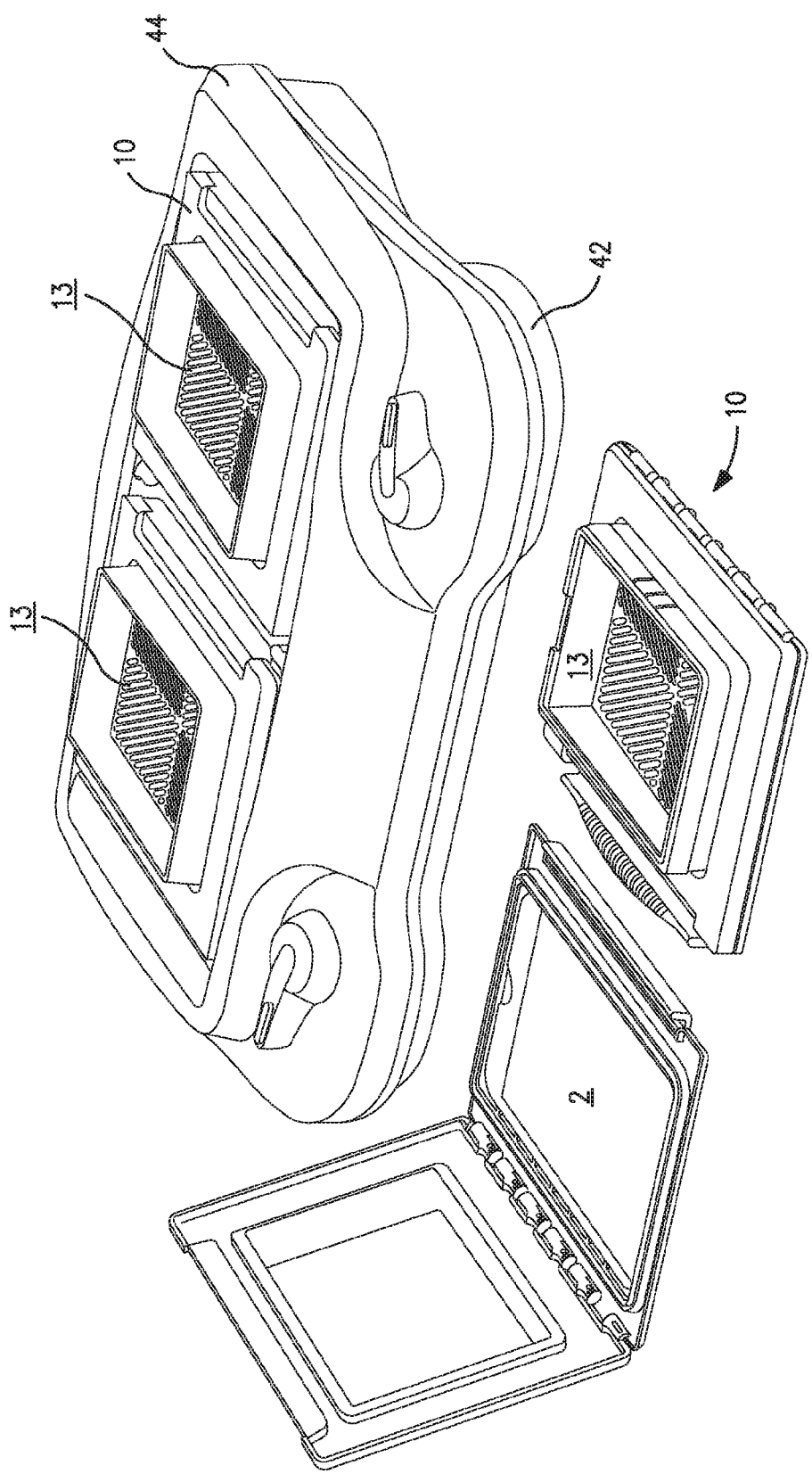

IMMUNOASSAY PRODUCT AND PROCESS

This application is a Continuation of U.S. patent application Ser. No. 13/468,258 filed May 10, 2012, which claims priority of provisional application Ser. No. 61/484,701 filed May 11, 2011, the disclosures of which are hereby incorporated by reference.

The embodiments disclosed herein relate to a device and process for the detection and position of substances that are contained in a blotting membrane. More particularly, it concerns a technique for applying reagents, wash solutions and detection chemistries to a blotting membrane to accomplish this detection quickly via the use of vacuum or positive pressure.

BACKGROUND

The use of gel electrophoresis is currently the ubiquitous technique for the separation of biological materials. Non-biological materials can also be separated using gels or other chromatographic supports as well, but the scope of effort with regard to biologicals is greater. Typical applications include separation of nucleic acid fragments of various sizes either in the context of sequence determination; in the detection of polymorphisms; or verification of sizes in other contexts. Also frequently conducted are separations of proteins, glycoproteins, protein fragments and application of gel separations as verification of homogeneity or purity, identification of post translational modifications and confirmation of molecular weight.

In all of these procedures, mixed samples of biological entities are applied to electrophoretic gels and the components are separated by application of an electric field across the gel. Regardless of the manner in which the gel is developed, the resulting pattern of migration of the substances contained in the sample must be detected in some manner.

To conduct this detection, typically the gel support is contacted with a blotting membrane to which the substances are transferred in the same pattern in which they appeared on the gel. The "spots" are then detected, at a minimum, by blocking the membrane with a protein or detergent solution to reduce non-specific binding (which otherwise leads to a high level of noise and low level of detection). Typical blocking agents include casein, bovine serum albumin (BSA), non-fat dry milk (generally about 1-5%) in a Tris buffer saline solution with TWEEN® surfactant (TBS-T solution) or phosphate buffer saline solution with TWEEN® surfactant (PBS-T solution). The biological entity is then incubated with an antibody specific for the antigen on the membrane. The membrane is then extensively washed to remove any contaminants, unbound blocking proteins or antibodies and the like. The membrane is then treated and incubated with a secondary enzyme-, radioisotope-, fluor-fluor-, or biotin-conjugated antibody specific for the primary antibody. The membrane is then extensively washed again to remove any unbound secondary antibody. Then a detection reagent, generally a chromogenic, chemiluminescent, fluorescent, radiological, or streptavidin-labeled material, is applied which either binds to, or is a substrate of the enzyme-conjugate. Lastly, the appropriate detection device is used to determine the presence, absence, position, quantity, etc. of the biological entity. The last six steps generally take from 3-6 hours to overnight depending on the speed of the reaction between the selected reagents, the membrane and the biological entity. The process requires multiple incubation periods of the membrane on a rocking or other suitable mixing platform. It is a lengthy process that most researchers dislike and which consumes (wastes) a large volume of reagents.

Some researchers have suggested the use of the capillary action of an absorbent material such as filter paper placed below the membrane to draw the remaining fluids through the membrane and improve the speed of the process especially the washing steps.

U.S. Pat. No. 5,155,049 mentions a system called the Hybrid-Ease® hybridization chamber marketed by Hoefer Scientific Instruments. This chamber is comprised two grids between which the membrane is sandwiched. The grid plates are snapped into position surrounding the membrane, and syringes fitted into the open space created by the grids. One syringe is used to apply reagents and wash, and the other to withdraw excess. The system requires large volumes of liquid in order to operate, is cumbersome to employ and is still quite time consuming. It also mentions that in some particular assays, such as ELISA assays, in small volume wells (such as 96 well microtiter plate), others have used vacuum to draw liquids through a membrane in a washing step. However, they discount this effort as it is only available in small volume applications and still is uncontrollable. They suggest instead that the better method is to use a manual press having the membrane on top of a filter paper and cover layer and then pressing the membrane sandwich between two plates to squeeze the liquid through the membrane and into the paper.

In U.S. Ser. No. 60/732,994, filed Nov. 3, 2005 it is suggested that one use a device formed of several layers including a porous support layer below the one or more layers of blotting membrane, a flow distributor above the blotting membrane(s) and a well on the flow distributor to contain the liquid to the desired area and to allow for lower starting volumes of such liquid. Preferably, the flow distributor is a non-binding or low binding porous membrane In co-pending U.S. Ser. Nos. 11/582,727 and 11/582,599 filed on Oct. 18, 2006, a device was disclosed in which a holder having a flow director and a porous support could be fit into a manifold apparatus to process the various fluids and detect the biological entity. The manifold has a cover with or without a well and a central opening inline with a central opening of the holder. While useful it has limitations that inhibit its universal use and acceptance.

It is clear that a more efficient method for detection of the biological materials or entities on blotting membranes is required. The embodiments disclosed herein permit a more effective and efficient detection of biological entities in a blotting membrane.

SUMMARY

In accordance with certain embodiments, an immunodetection system and method are provided. The system comprises a manifold base adapted to communicate with a driving force such as vacuum. The manifold holds a carrier that supports a blot membrane holder. The blot membrane holder holds the blot membrane to which proteins can be bound by way of electrophoresis. The system and method enable users to quickly and efficiently prepare protein blots for detection such as by chemiluminescence.

In one embodiment, there is provided an apparatus useful in conducting the method disclosed herein. The device is comprised of a blotting membrane holder (also referred to as a blot holder, or simply as a holder) formed of a lower porous support layer and an upper flow distributor. The two are held together by a method such as by a hinge, clips, elastic bands, adhesives, ball and socket, pins and recesses, or cooperatively engaging fasteners or other such means. The holder is opened and one or more blotting membranes are placed between the lower and upper layers. The holder is then closed and placed into a carrier formed of an upper and lower plate, each with at least one opening that allows fluid to pass through the top plate of the carrier, through the holder and membranes contained within it, and then through the lower plate of the carrier. The carrier is then set into the manifold apparatus to process the samples on the blotting membrane. Upon completion of the process, the carrier is removed from the manifold, opened, and the blot membrane holder is removed. The blot membrane holder is then opened and the blot membrane is extracted for downstream detection.

In another embodiment, the holder is formed of a material selected from the group consisting of plastic and paper, the holder has a top portion and a bottom portion, each top and bottom portion has an outer edge, a top surface and a bottom surface and a thickness between the top and bottom surfaces, at least one of the portions has a solid portion inward of the outer edge, at least the top portion has an opening inward of the outer edge, a porous support formed on the top surface of the bottom portion and a flow distributor formed on a lower surface of the top portion which distributor covers the opening of the top portion wherein the holder has a means for releasably securing the first and second portions to each other when the top and bottom portions of the holder are aligned such that the bottom surface of the top portion and the top surface of the bottom portion are aligned and arranged adjacent each other to bring the top and bottom portions together.

In another embodiment, the holder is formed so that the top and bottom portions each has a perforation along one side and the perforation is aligned on the top and bottom portions, and the perforations are easily torn to open the holder to retrieve the blot membrane In one embodiment, the carrier has an outer perimeter wall extending upwardly from the opening of the top plate of the carrier to form a well to hold reagents and washing fluids.

In a further embodiment, a carrier has one or more level indicators to indicate whether the top surface of the carrier is level in the horizontal plane along at least its length and preferably along its length and width. The level also could be on the manifold In another embodiment, the level indicator is a single 360 degree bubble indicator.

In a further embodiment, the level indicators are at least two line level bubble indicators with at least one arranged along the length of the top surface of the top plate and at least one arranged along the width of the top surface of the top plate.

In a further embodiment, the carrier inner surface(s) contains a feature to stretch the one or more blotting membranes in the holder so as to avoid the formation of wrinkles in the membrane and make the surface of the membrane flat or planar as possible.

In another embodiment, the carrier has a stretching feature formed of a flange seal located on at least one of the inner surfaces of the top or bottom plates. Preferably it has a flange seal formed on at least the adjacent inner surfaces of the bottom plate. More preferably, the flange seals are located at a width and length that is greater than the opening of the holder but less than the width and length of the outer edge of the holder.

In another embodiment, the carrier has a stretching feature consisting of a compressible or flexible member positioned on one half of the carrier with an opposing raised rigid feature on the other half of the carrier.

In one embodiment, the manifold is subdivided into two or more subwells to run parallel blotting membranes or subparts of one blotting membrane, each membrane is typically processed with at least one different reagent.

In another embodiment, the carrier is subdivided into two or more subwells with the holder also subdivided into corresponding subwells.

In another embodiment, the carrier subwells are individually sealed and aligned with the corresponding holder subwells so as to prevent fluid migration between wells.

In another embodiment, the manifold has leveling feet that when used in conjunction with one or more level indicators of one embodiment of the carrier allow the manifold and carrier to be leveled in a horizontal plane.

In one embodiment, the manifold has a series of feet that are capable of being adjusted in a vertical direction so as to level the manifold in relation to the level indicator(s) on the carrier when the carrier is attached to the manifold.

In further embodiment, the series of feet have a screw that fits into a threaded portion of the manifold bottom to allow the feet to be individually raised or lowered in a vertical direction.

In another embodiment, the manifold is subdivided into two or more subwells to run parallel carriers with different blotting membranes or subparts of one blotting membrane, each membrane is typically processed with at least one different reagent.

In another embodiment, the carrier top plate opening has a lid positioned onto the upper edge of the opening to minimize evaporation during long term, i.e. overnight incubation.

In another embodiment, the lid has a resealable relation with the well.

In another embodiment, the lid is light blocking such as being made from an opaque material.

In another embodiment, the opening on the carrier bottom plate has a cover to prevent fluid leakage.

In another embodiment, the cover is releasably sealed.

In another embodiment, the cover has a valve feature.

In another embodiment, the valve is of a duck bill or umbrella configuration.

In another embodiment, the valve is operational by a pressure differential and closed when no pressure differential is present across the valve.

In another embodiment, a rapid, efficient and convenient method to detect one or more biological entities on a blotting membrane is provided. The detection can relate to the position, nature or amount of the biological substance on a membrane. The method involves a pressure assisted regiment, selected from positive pressure or a vacuum for the supply and removal of reagents to and from the blotting membrane and permits washing of the contaminants from substances embedded in the membrane that are to be detected using very low volumes of liquid and reagents. This method enables completion of the blocking, washing and antibody binding steps in about 30-45 minutes without compromising blot quality. One simply takes a holder, opens it and places the blotting membrane(s) on one of the surfaces such that the lower surface of the blotting membrane is adjacent the porous support and the upper surface of the blotting membrane is adjacent the flow distributor when the device is closed around the membrane(s). The device is placed on or in a manifold having a pressure or vacuum supply and the process is commenced.

It is another object of the embodiments disclosed herein to provide an apparatus for conducting pressure or vacuum assisted immunoassays of one or more blots comprising a vacuum manifold, a carrier designed to fit on the manifold and a holder designed to fit within the carrier for processing the blots and a mean of collecting one or more of the antibodies.

It is a further object of the embodiments disclosed herein to provide a process for conducting vacuum assisted immunoassays on one or more membranes comprising the steps of:
  a. providing a vacuum manifold, a carrier for holding a holder, the carrier being formed of a top plate and a bottom plate each with at least one opening formed through its thickness to allow fluid to flow through it, a holder for the one or more blotting membranes, the holder being capable of being positioned between the top and bottom plates of the carrier and being in fluid communication with the at least one opening of each plate of the carrier, the holder being formed of a porous support and a flow distributor which are held together, one or more membranes containing one or more biological entities to be assayed, the membrane(s) being placed on the porous support, a flow distributor being on top of the membrane and the holder being placed between the top and bottom plates of the carrier such that the flow distributor is adjacent the bottom or inner surface of the top plate and the porous support is adjacent the inner of top surface of the bottom plate,
  b. adding one or more reagents to the at least one opening of the carrier top plate and applying a vacuum to pull the reagents into the membrane through the opening in the top plate, the flow distributor and porous support of the holder and the opening of the bottom plate, and
  c. adding one or more washing agents to the one or more wells and applying a vacuum to pull the washing agents and any unbound reagents through the top plate opening, flow distributor, membrane and porous support and opening of the bottom plate of the carrier and into the vacuum manifold and
  d. repeating steps (b and c) one or more additional times as desired or required.

In certain embodiments, disclosed is a device for conducting immunoassays comprising a holder formed of a material selected from the group consisting of plastic and paper, the holder having a top portion and a bottom portion, each top and bottom portion having an outer edge, a top surface and a bottom surface and a thickness between the top and bottom surfaces, at least one of the portions has a solid portion inward of the outer edge, at least the top portion has an opening inward of the outer edge, a porous support formed on the top surface of the bottom portion and a flow distributor formed on a lower surface of the top portion which distributor covers the opening of the top portion, wherein the holder has a means for releasably securing the first and second portions to each other when the top and bottom portions of the holder are aligned such that the bottom surface of the top portion and the top surface of the bottom portion are aligned and arranged adjacent each other to bring the top and bottom portions together.

In certain embodiments, the means for releasably securing may comprise a sealing material formed outwardly and circumscribing the porous support opening. The top and bottom portion of the holder may be made of one piece of material and the holder may have a fold running a width of the holder to form a first portion and second portion. The fold may be a hinge.

In certain embodiments, the flow distributor may have a lower and an upper surface and the upper surface of the flow distributor may be attached to the bottom surface of the top portion of the holder such that the thickness of the first portion forms one or more wells on the upper surface of the flow distributor. The opening of the top portion is centrally located within the outer edge of the top portion.

In certain embodiments, the device for conducting immunoassays may comprise a holder and a carrier for the holder, the holder being formed of a material selected from the group consisting of plastic and paper, the holder may have a top portion and a bottom portion, each top and bottom portion may have an outer edge, a top surface and a bottom surface and a thickness between the top and bottom surfaces, at least one of the portions may have a solid portion inward of the outer edge, at least the top portion may have an opening inward of the outer edge, a porous support formed on the top surface of the bottom portion and a flow distributor formed on a lower surface of the top portion which distributor covers the opening of the top portion wherein the holder may have a means for releasably securing the first and second portions to each other when the top and bottom portions of the holder are aligned such that the bottom surface of the top portion and the top surface of the bottom portion are aligned and arranged adjacent each other to bring the top and bottom portions together.

In certain embodiments, the device also may comprise a carrier for the holder comprised of a top plate and a bottom plate, each having a width and a length, a top and bottom surface and a thickness between the top and bottom surfaces, an outer edge and at least one opening, the plates being of a length and width greater than the length and width of the holder, the top plate of the carrier having an opening substantially equal in width and length to the opening of the top portion of the holder, the bottom surface of the top plate and the top surface of the bottom plate each having one or more seals in alignment with each other when the two plates are adjacent each other and the seals being arranged on each surface at a width and length greater than that of the opening of the top plate, but less than the outer dimensions of the holder, at least one of the plates has a seal formed adjacent the outer edge of the plate and outward of the seal of that plate, and a means for releasably holding the top and bottom plate together.

In certain embodiments, the seals in the bottom surface of the top plate and the top surface of the bottom plate may be flange seals.

In certain embodiments, there may be at least one level indicating device attached to the upper surface of the top plate, and it may include a 360 degree indicator. There may be two level indicators, one along the length and the other along the width of the top surface of the top plate.

In certain embodiments, disclosed is a device for conducting vacuum assisted immunoassays comprising a vacuum manifold and a holder formed of plastic or paper, the holder has a fold running a width of the holder to form a first portion and second portion, each portion has an opening that are aligned when the holder is folded closed along the fold, a porous support covers a first opening and a flow distributor covers the second opening wherein the holder has a means for releasably securing the first and second portions to each other when the holder is folded closed along the fold to bring the first and second portions together. The flow distributor may be a membrane.

In certain embodiments, disclose is a device for conducting immunoassays comprising a vacuum manifold having a base, the base having an upper support surface for supporting one or more carriers that contain a holder to be processed and a drain below the support, the upper surface containing one or more central openings extending through it and the one or more central openings are in alignment with the one or more carriers.

BRIEF DESCRIPTION OF THE DRAWINGS

FIG. 3 is a perspective view of a carrier in a closed position in accordance with certain embodiments;

FIG. 4 is a perspective view, shown in cross-section, of a carrier in accordance with certain embodiments;

FIG. 10A is a perspective view of a manifold, holder and carrier in accordance with certain embodiments.

DETAILED DESCRIPTION

Figure 1:
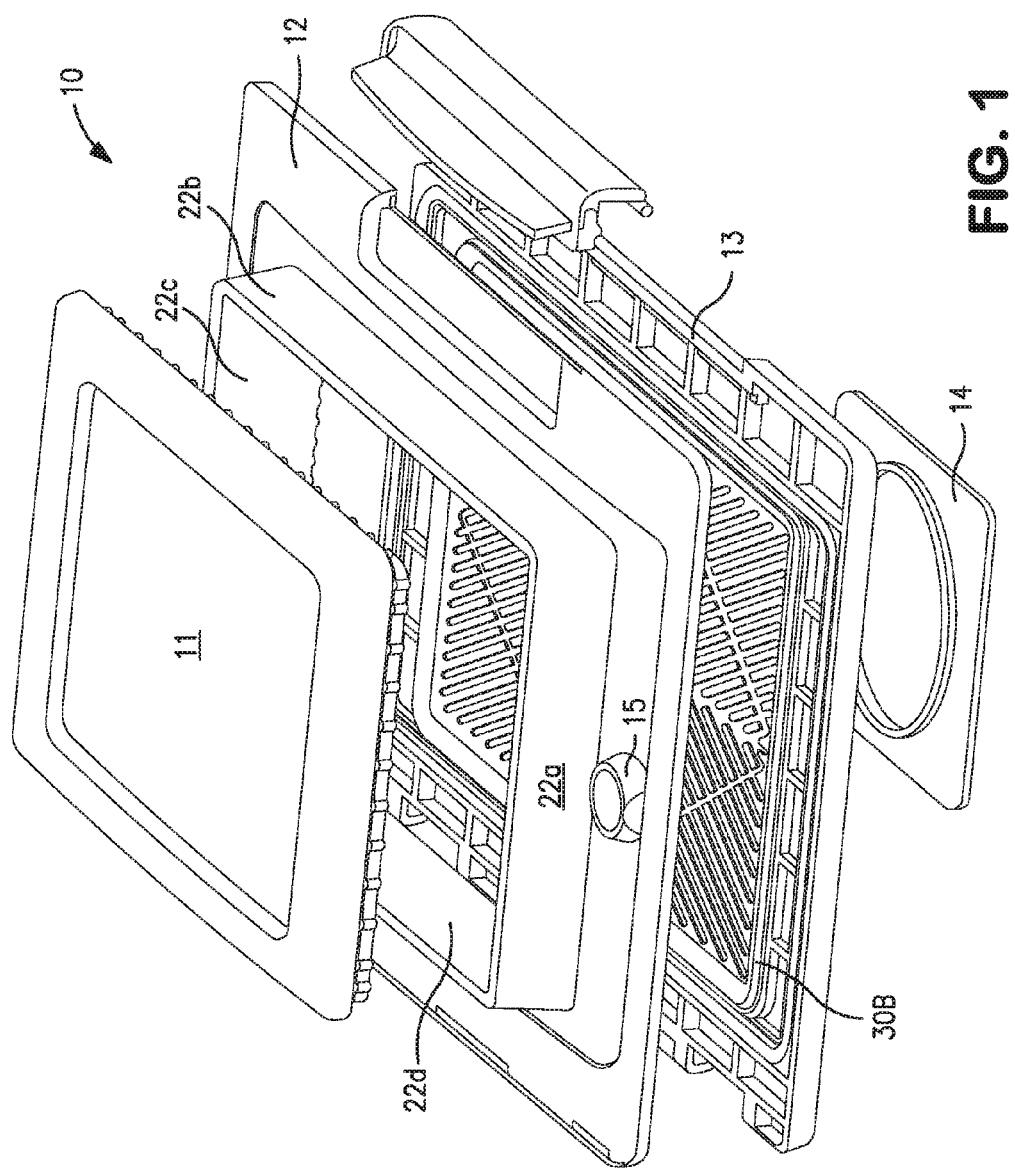
FIG. 1 is an exploded view of a carrier in accordance with certain embodiments.

Turning first to FIG. 1, there is shown a carrier 10 in accordance with certain embodiments. In the embodiment shown, the carrier 10 includes a lid 11, a carrier top plate 12, a carrier bottom plate 13, a cover 14, and a bubble level 15 on the carrier top plate 12. In accordance with certain embodiments, the carrier 10 serves to hold the blot holder flat and to deliver reagents such as antibodies, wash buffer, etc. to the blot holder. In accordance with certain embodiments, the carrier 10 is a standalone device, separate from a manifold base (discussed below), which allows the user to setup multiple blots at the same time. Thus, each carrier 10 can be selectively loaded with blot holders containing blots, their respective antibodies added, and then incubated.

Figure 2:
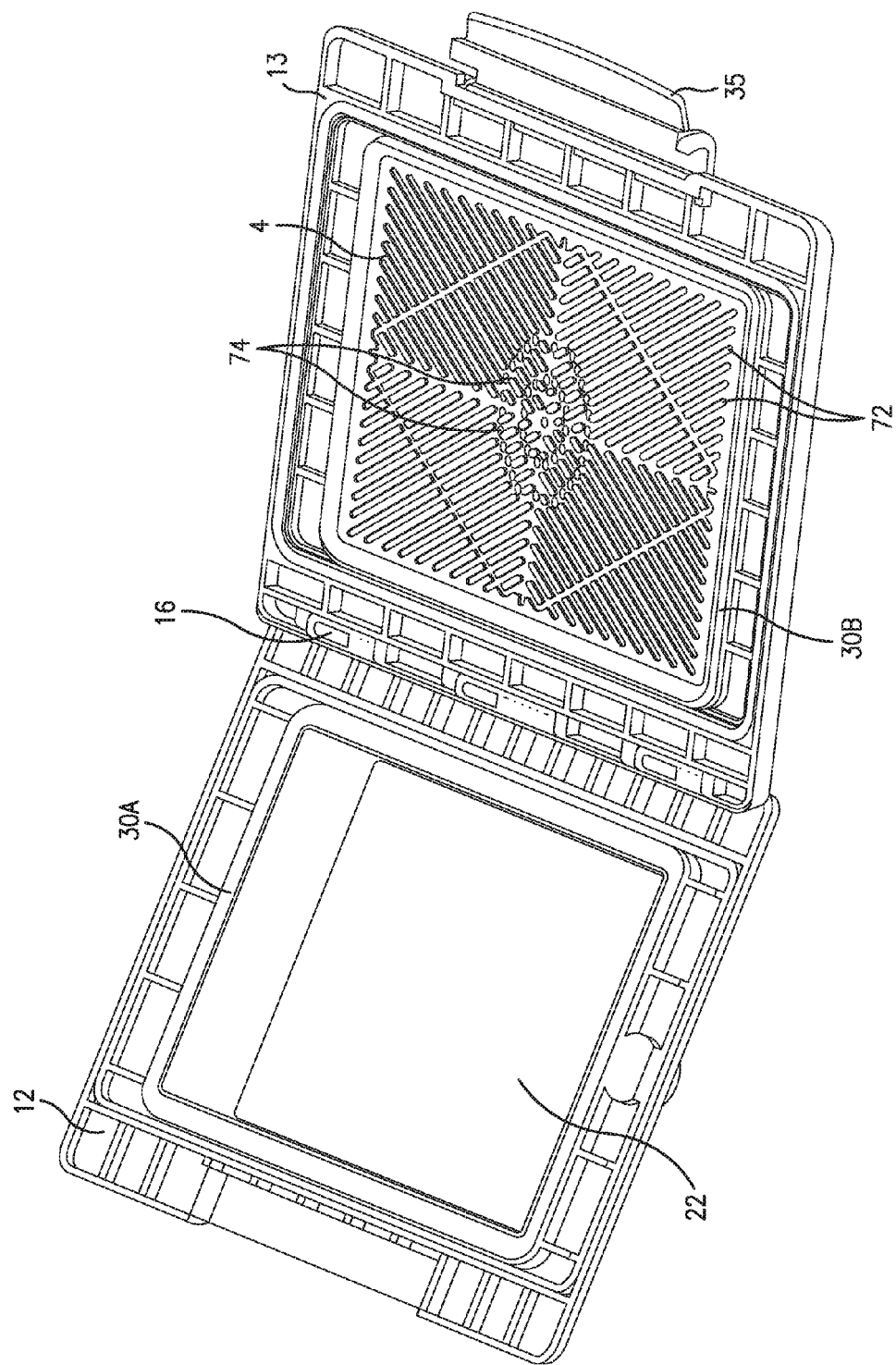
FIG. 2 is a perspective view of a carrier in an open position in accordance with certain embodiments.

FIG. 2 shows an embodiment of the carrier 10 in an open position, with the underside of the top plate 12 shown to the left in the drawing and the top side of the bottom plate 13 shown to the right. In the embodiment shown, the top plate 12 and bottom plate 13 are hingedly connected at 16. As shown in this embodiment the hinge is a "live" hinge that bonds the two portions together. Alternatively, the hinge could be made separately and attached using adhesives, heat bonds or mechanical fasteners. Other embodiments use no hinge (not shown) and use clips, elastic bands or cooperatively engaging fasteners such as a slot and detent, friction fit pin or the like form on or in the respective top and bottom portions to hold them together during use. Other comparable means will be obvious to one of skill in the art and it is meant to include them as well.

In accordance with certain embodiments, the carrier top plate 12 may either have one or more wells 22, which can be used for holding and/or delivering washing fluids and reagents during use. The well(s) 22 may either be formed as part of the top surface of the top carrier plate 12 with upstanding walls 22a, 22b, 22c and 22d (FIG. 1), or as a separate piece which is simply attached or placed on top of the carrier top plate 12. The lid 11 can be placed on the carrier 10 to cover the well 22 and prevent antibodies and other fluids from evaporating during extended incubation periods, particularly during overnight incubation.

The carrier bottom plate 13 includes a porous support 4 that may be a simple screen, a grid, a flow directing grid or a sintered porous structure such as a POREX® membrane or a coarse or large pored microporous filter, such as a woven or non-woven paper, a polypropylene or polyethylene fabric, a glass mat or paper, or a 1-10 micron microporous filter. Such supports can be made of polymer, glass, ceramic or metal materials including but not limited to metals, such as stainless steel or steel alloy, aluminum and the like, and polymers such as polyethylene, polypropylene, polysulfone, polyethersulfones, styrenes, nylons and the like. FIG. 2 shows a porous support 4 in the form of a flow directing grid including a series of grooves 72 and openings 74. The openings 74 are inwardly positioned from the perimeter of the porous support 4. The openings 74 are in fluid communication with the grooves 72 so that fluid is collected in the grooves 72 and directed through the openings 74. The grooves 72 collect and deliver the spent fluid to the openings 74 which direct the fluid to a waste chamber or collection tray (not shown). If the researcher wishes to collect one or more of the fluids, then a collection tray can be appropriately positioned to do so. Those skilled in the art will appreciate that other patterns of grooves or openings may be used, as the desired outcome is to direct the spent fluids to an opening or a series of openings that direct the spent fluids to a predetermined destination.

The outer edges of the support 4 and the carrier top plate 12 may be made of the same materials as the support 4. When an integral hinge is used, it must be made of a flexible material such as polyethylene, polypropylene, an elastomer or one of the impact modified materials such as ABS, K-resin and the like. When a separate hinge, clips, elastic bands, adhesive film or other securing means are used they may be made of metal, plastic or elastomers as desired.

In accordance with certain embodiments, a first flange seal 30A is positioned on the underside of the top carrier plate 12 as shown, and cooperatively with a second flange seal 30B positioned about the porous support 4 on the carrier bottom plate 13, maintains a fluid tight system when the top and bottom plates are in the closed position with the blot holder engaged. Thus, the flange seals 30A and 30B are positioned so that when the top carrier plate 12 is rotated with respect to the bottom carrier plate 13 to a closed position, the two seals register or align with one another to seal the carrier. In certain embodiments, each flange seal 30A, 30B is preferably made of a flexible elastomer such as silicone, or thermoplastic elastomer (TPE) and is V-shaped, with one leg of the V being short than the other. The long end of each V-shaped flange seal seats in a respective recess of the top and bottom carrier plates (FIG. 4). The short leg of each V-shaped seal is a raised, easily deformable feature. In the carrier closed and sealed position, the shorter legs of the V on the top carrier plate will contact the top surface of the blot holder. The shorter leg of the V on the bottom carrier plate will contact the bottom of the blot holder and deflect as best seen in FIG. 4. The angled geometry of the seal exerts a force to pull or stretch the holder 50 when deflected, which "drums" the membrane and keeps it flat. A flat membrane avoids deformities that can create peaks and valleys on the membrane surface which pools the antibody volume, which in turn leads to areas of the blot membrane having more or less exposure to the antibodies, resulting in poor and inconsistent results. This seal prevents leaking and enables long term (e.g., overnight) incubation. The design of the seal also allows for a low force sealing mechanism and low clamp force required for the carrier 10. This helps to maintain flatness of the holder and the blot membrane. A releasable latch 35 or other locking mechanism locks the carrier in the closed position (FIG. 3). In accordance with certain embodiments, a single flange seal can be used, preferably the flange seal 30B for the bottom plate. The bottom flange seal 30B functions to stretch the blot holder. Once stretched, the interface is designed so that the carrier top and bottom pinch the blot holder in place. Outer flange seals 300A, 300B are also shown in FIG. 4.

Figure 5:
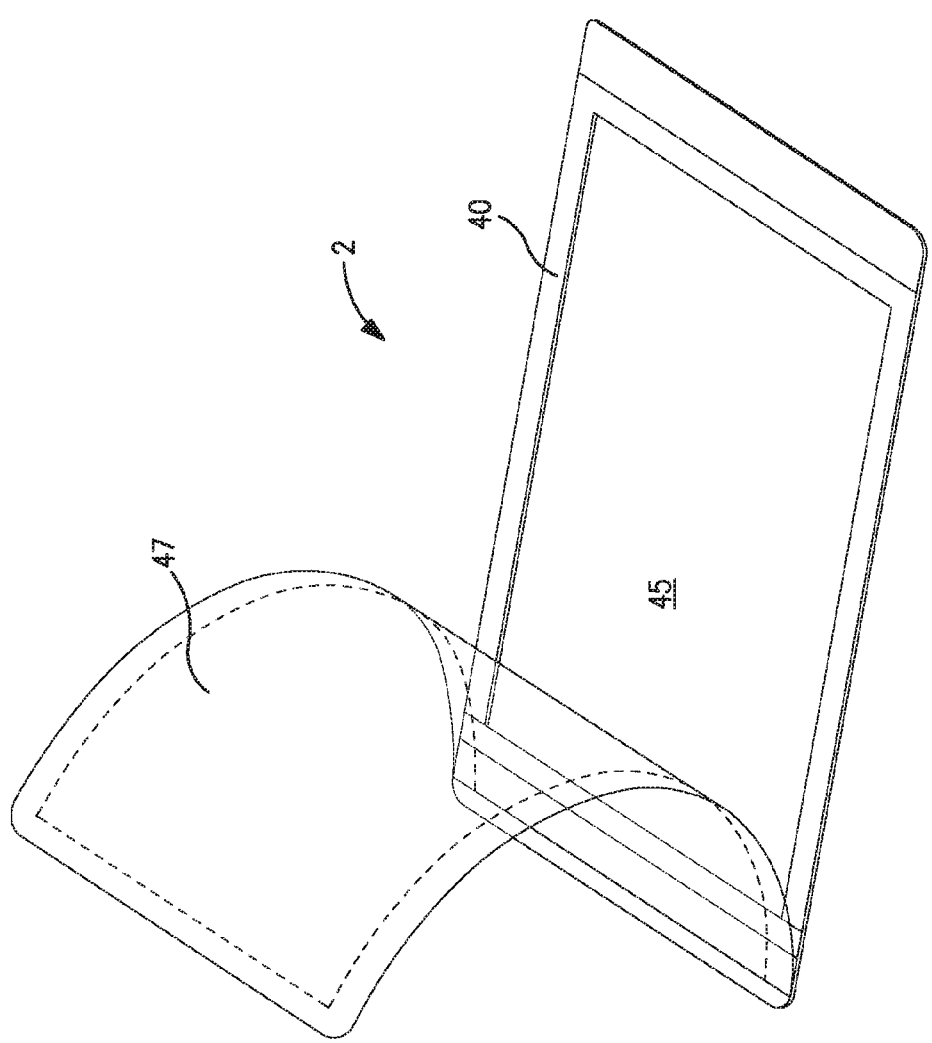
FIG. 5 is a perspective view of a blot membrane holder, including a blotting membrane, in accordance with certain embodiments.
Figure 5A:
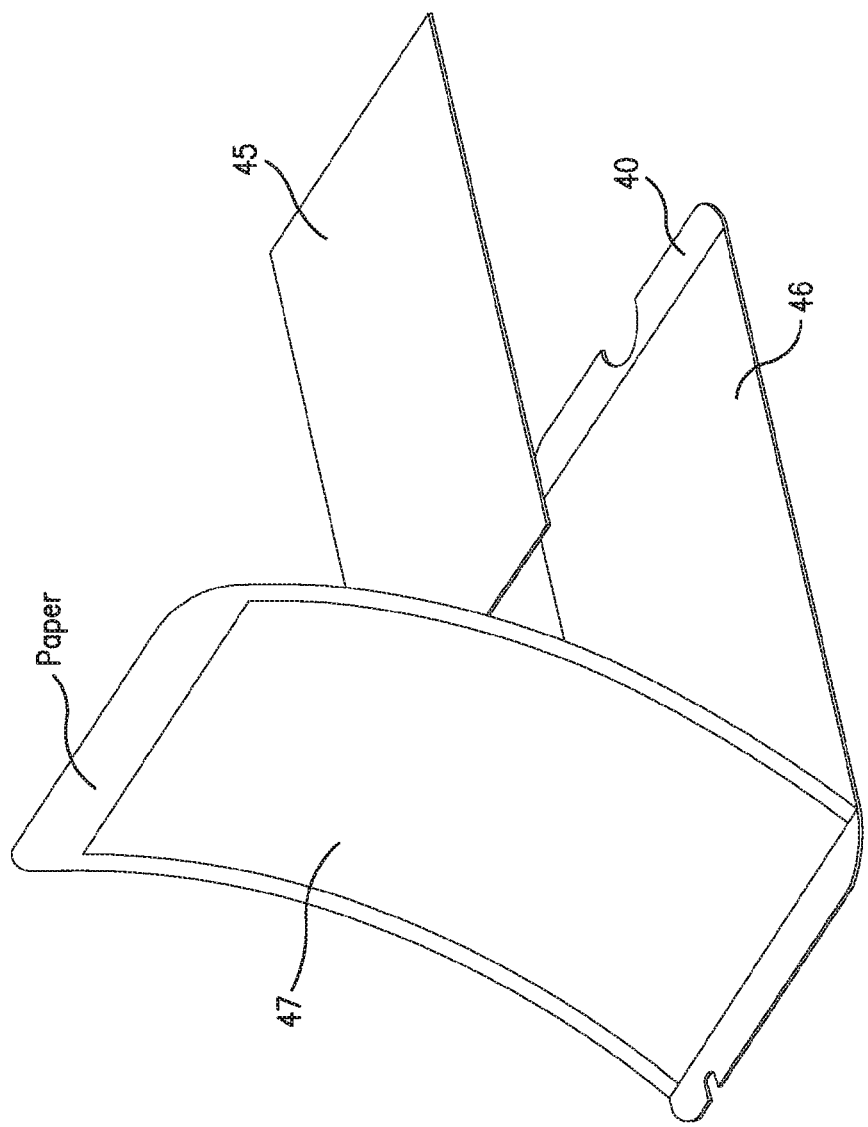
FIG. 5A is a perspective view of a blot membrane holder, showing a flow distributor, in accordance with certain embodiments.
Figure 5B:
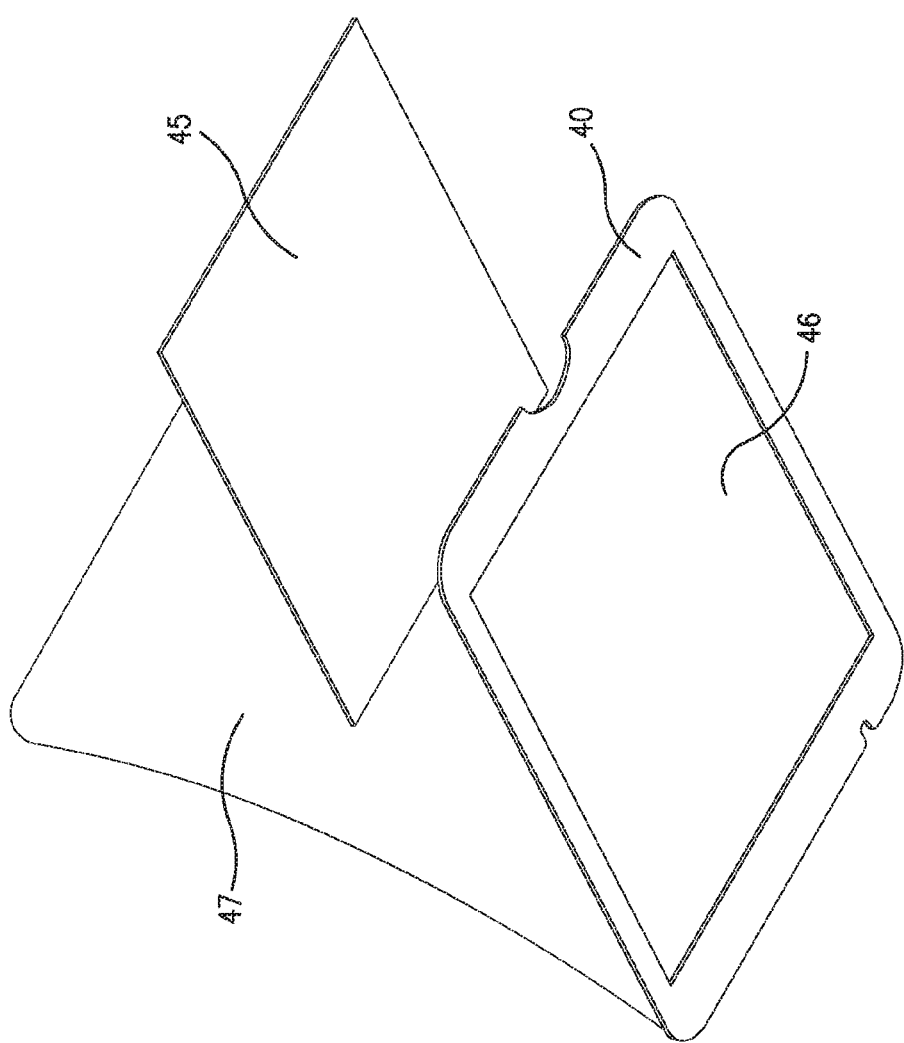
FIG. 5B is a perspective view, viewed from the underside, of a blot membrane holder, in accordance with certain embodiments.
Figure 6:
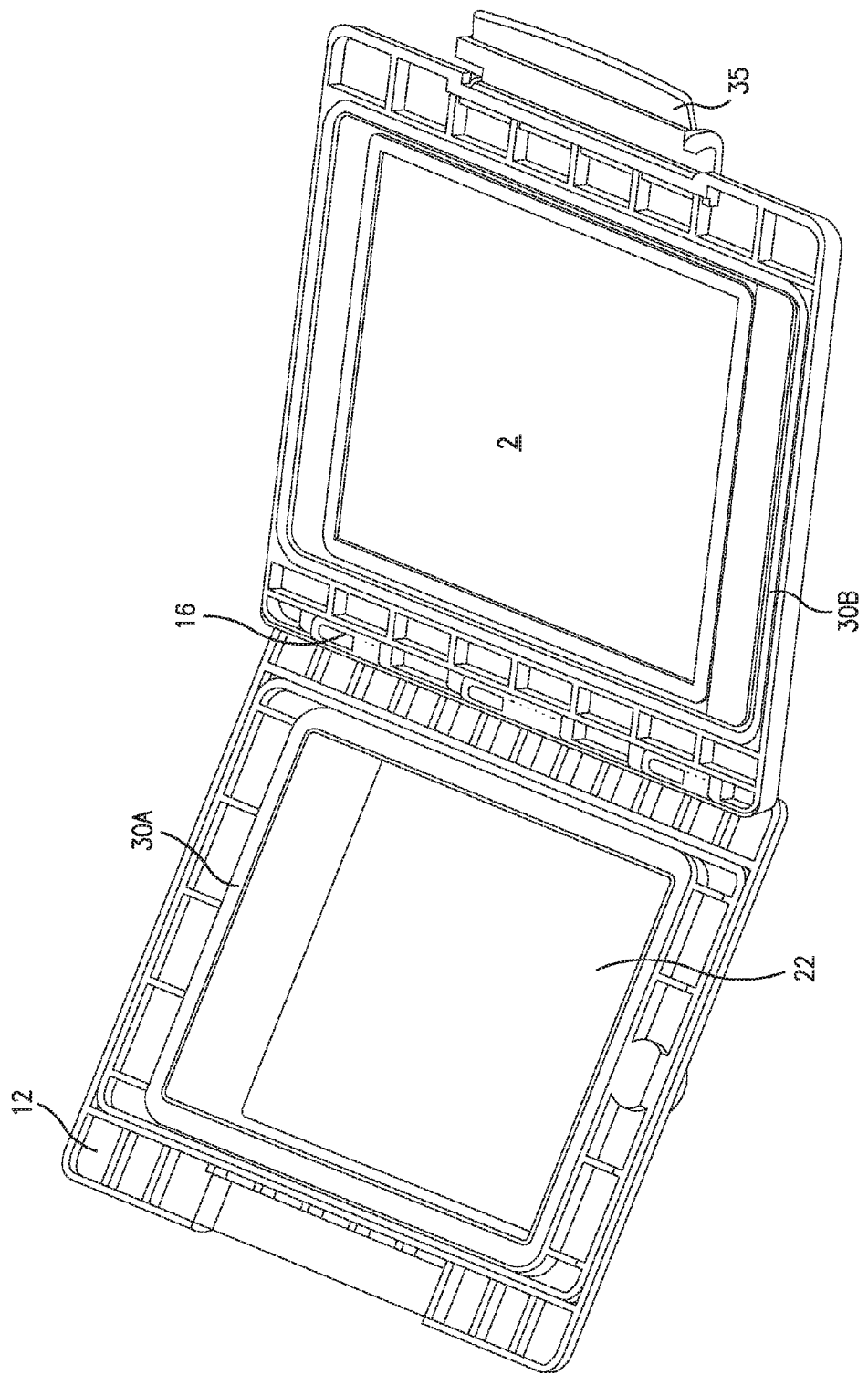
FIG. 6 is a perspective view of a carrier in an open position, including the holder of FIG. 5, in accordance with certain embodiments.

FIGS. 5, 5A and 5B show a holder 2 in accordance with certain embodiments. The holder 2 includes a frame 40 having a perimeter edge configured to support a protein blotting membrane 45. In certain embodiments, the frame 40 is constructed of plastic or paper. In certain embodiments, the material of the frame 40 can be bioresin, cardboard, HIPS, paper, or any other suitable rigid material that can support the membrane and keep it flat. In accordance with certain embodiments, a flow distributor 46, such as a GVPP membrane, is laminated or otherwise attached to the frame, and over which the blotting membrane 45 can be positioned. The flow distributor 46 is attached to the frame and the blot membrane is sandwiched between the flow distributor 46 and the porous support 47 when the blot holder is closed. The porous support 47 on the blot holder is supported and in contact with the porous support 4 of the carrier bottom plate. The flow distributor 46 functions to evenly distribute the blocking solution and the antibodies over the blot membrane. It also regulates flow through of these solutions when vacuum is applied. The holder 2 also includes a porous support 47, such as a piece of polypropylene non-woven mesh bound to the frame along one edge, allowing easy access for the user to add the blot membrane, and which supports the blot membrane and protects it from damage under vacuum force. The support 47 is porous to allow free flow of liquids through the blot holder 2. The holder 2 is shown properly positioned in the carrier 10 in FIG. 6.

In certain embodiments, the holder 2 can be made by laminating a pressure sensitive adhesive to the back of a polypropylene mesh such that after adding the blot membrane to the holder, the user removes a backing strip to expose the pressure sensitive adhesive and then seals the mesh to the flow distributor (e.g., to the GVPP membrane) to create a sealed envelope. To remove the blotting membrane, perforations and zippers can be included to tear open the envelope.

In certain embodiments, a thin patapar paper, wax paper or other thin sheet of paper material is laminated to one side of a polypropylene mesh. When the holder is wet with water (as is required in the process), the wet paper backing sticks to the GVPP membrane, creating a temporary seal. After the process is complete, the blot membrane is easy to remove without having to tear anything or manage sticky adhesives. The holder is then disposed of, as after the paper backing dries, it curls and the holder becomes unusable.

Figure 7:
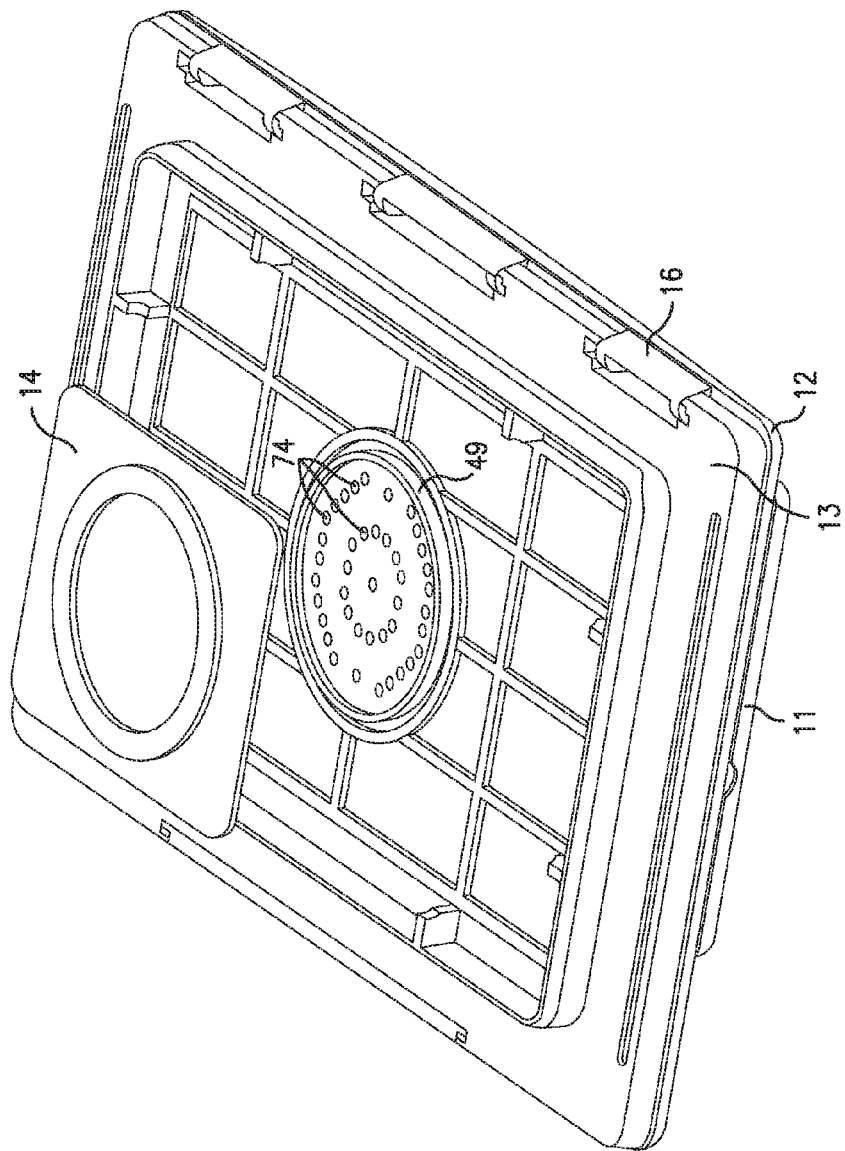
FIG. 7 is an exploded perspective view of the underside of the carrier in accordance with certain embodiments.
Figure 8:
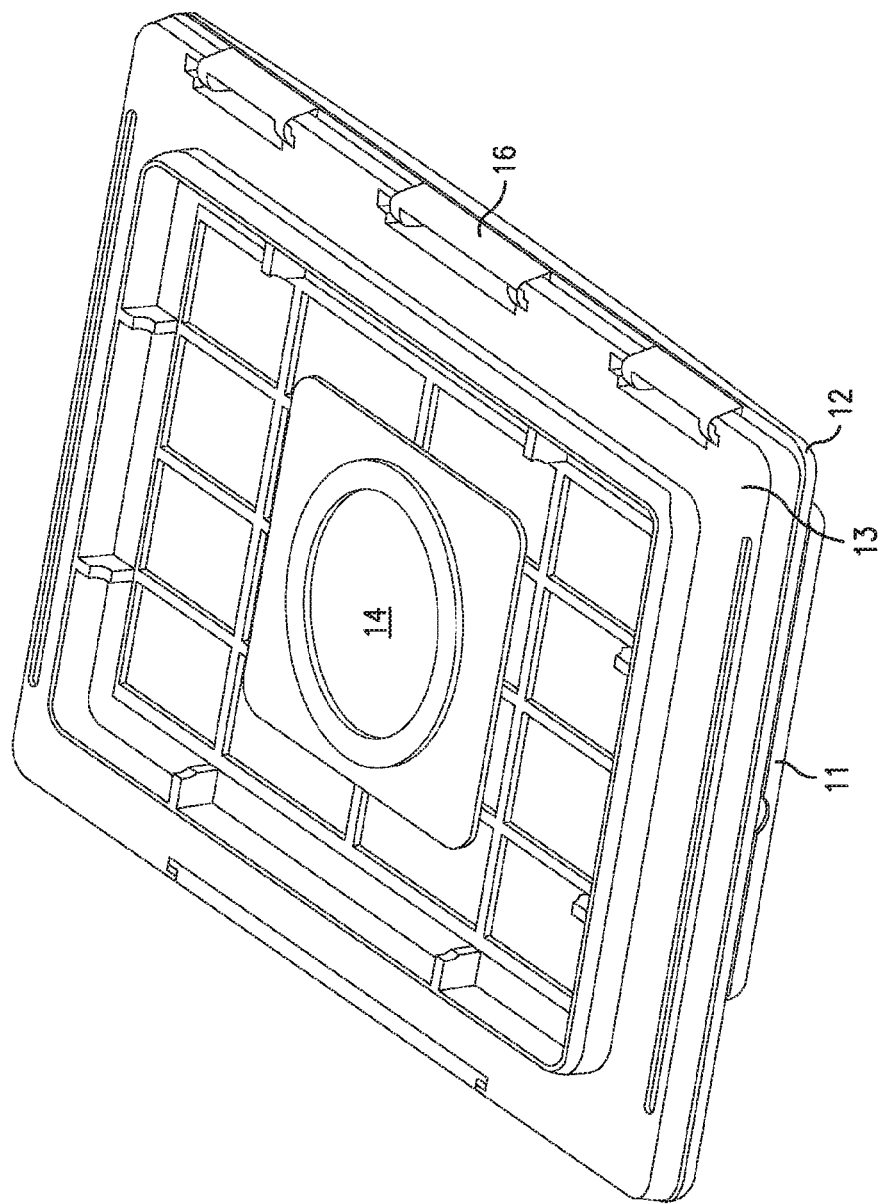
FIG. 8 is a perspective view of the underside of the carrier with the cover in place, in accordance with certain embodiments.

FIGS. 7 and 8 illustrate the underside of the bottom carrier plate 13. Visible in FIG. 7 are the plurality of openings 74 in the porous support 4. Cover 14 is used to cover the openings to prevent leaking of antibodies during incubation, particularly when incubating for long periods of time, such as overnight, as seen in FIG. 8. In accordance with certain embodiments, the openings 74 are surrounded by an annular raised ring 49, and the cover 14 has a corresponding annular slot 60 (FIG. 4) configured to mate with the annular ring 49 and thus the cover can be pressed onto the ring to secure it to the carrier plate 13.

Figure 4A:
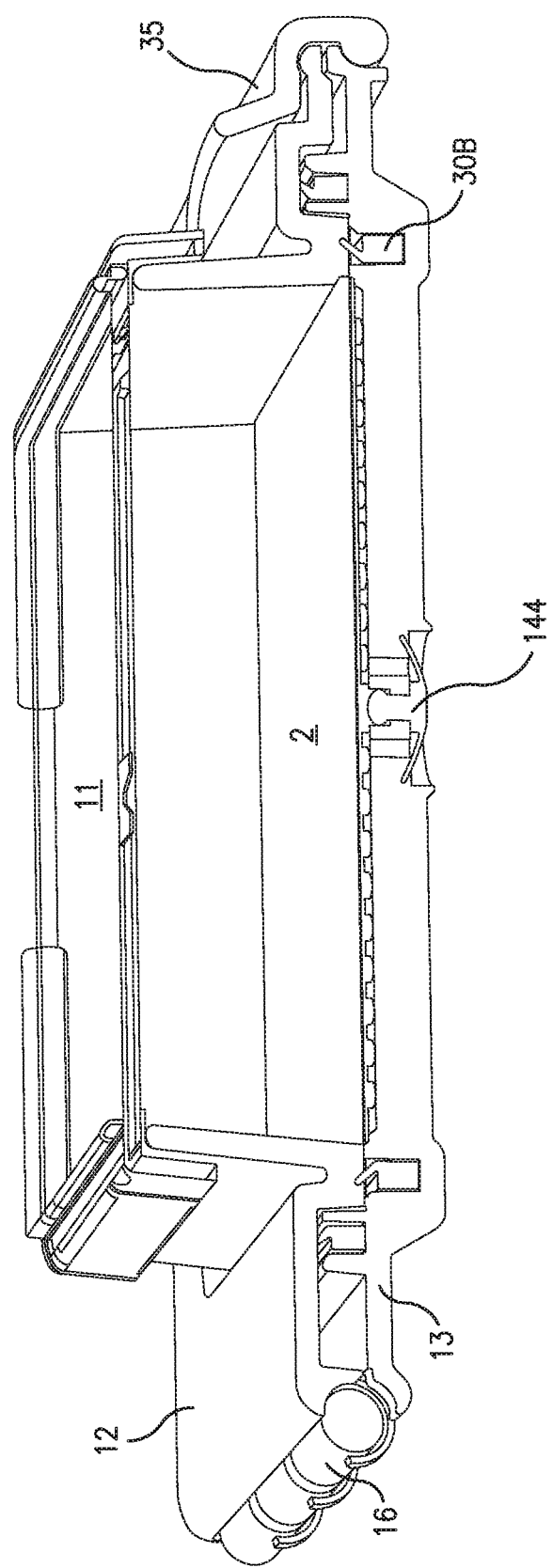
FIG. 4A is a perspective view, shown in cross-section, of a carrier with an umbrellas valve in accordance with certain embodiments.

Alternatively, the cover 14 can be eliminated, and an umbrella valve 144 can be used to retain the liquid during incubation, as shown in FIG. 4A. When the vacuum is turned on, the valve opens and the liquid drains. Preferably the valve is made of EPDM (ethylene propylene diene monomer) due to its stiffness and ability to snap closed quickly when the vacuum is turned off. This helps to prevent backpressure and air trapping, which (with the silicone valves) was causing the blot holder to bow and lead to adverse antibody pooling. Antibody pooling (non uniform coverage) leads to a non-uniform signal on the final blot readout-areas near the trapped air will have a weak signal (faint) and areas with pooled antibody will have a strong signal (bold).

Figure 9:
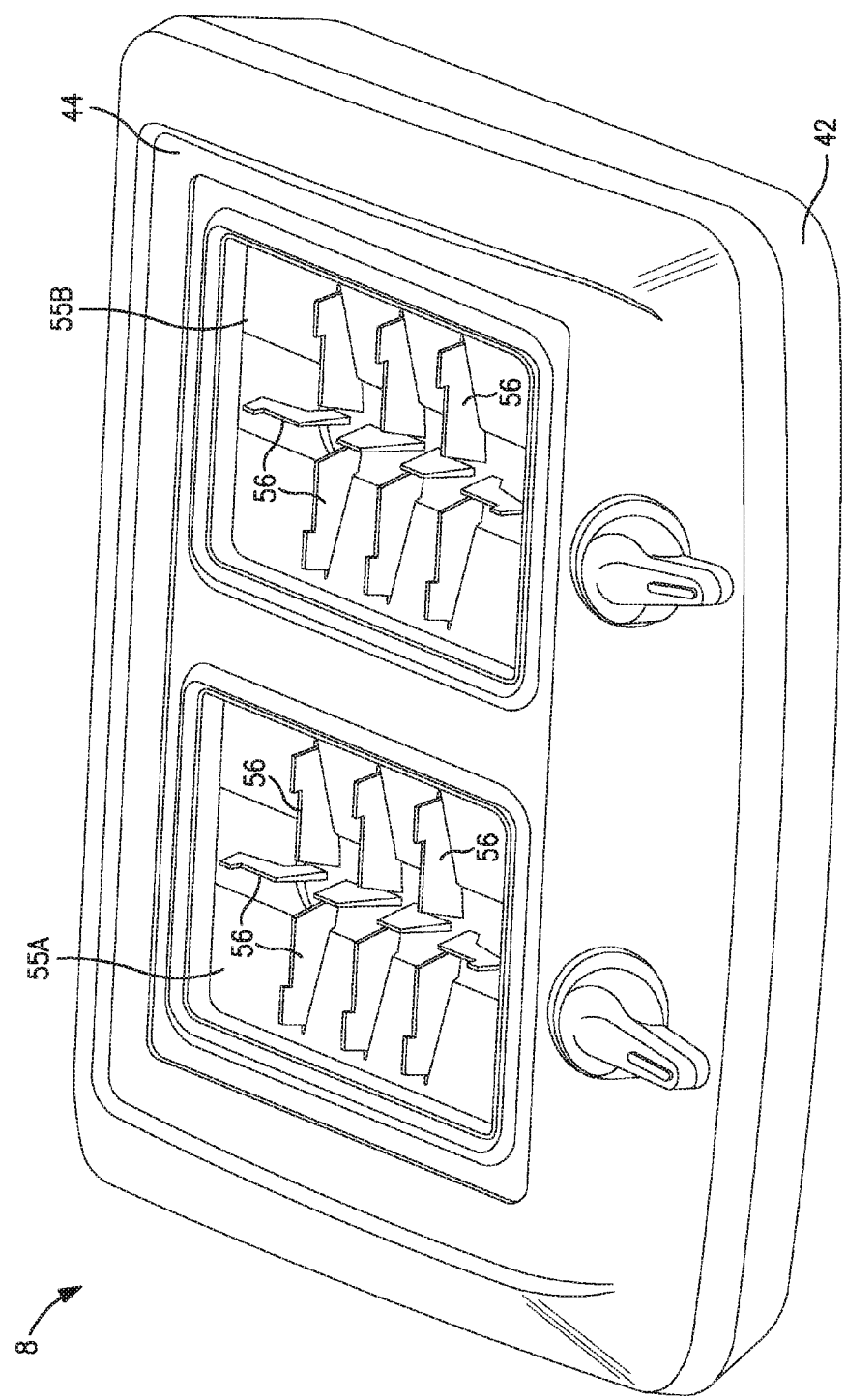
FIG. 9 is a perspective view of a manifold in accordance with certain embodiments.
Figure 10:
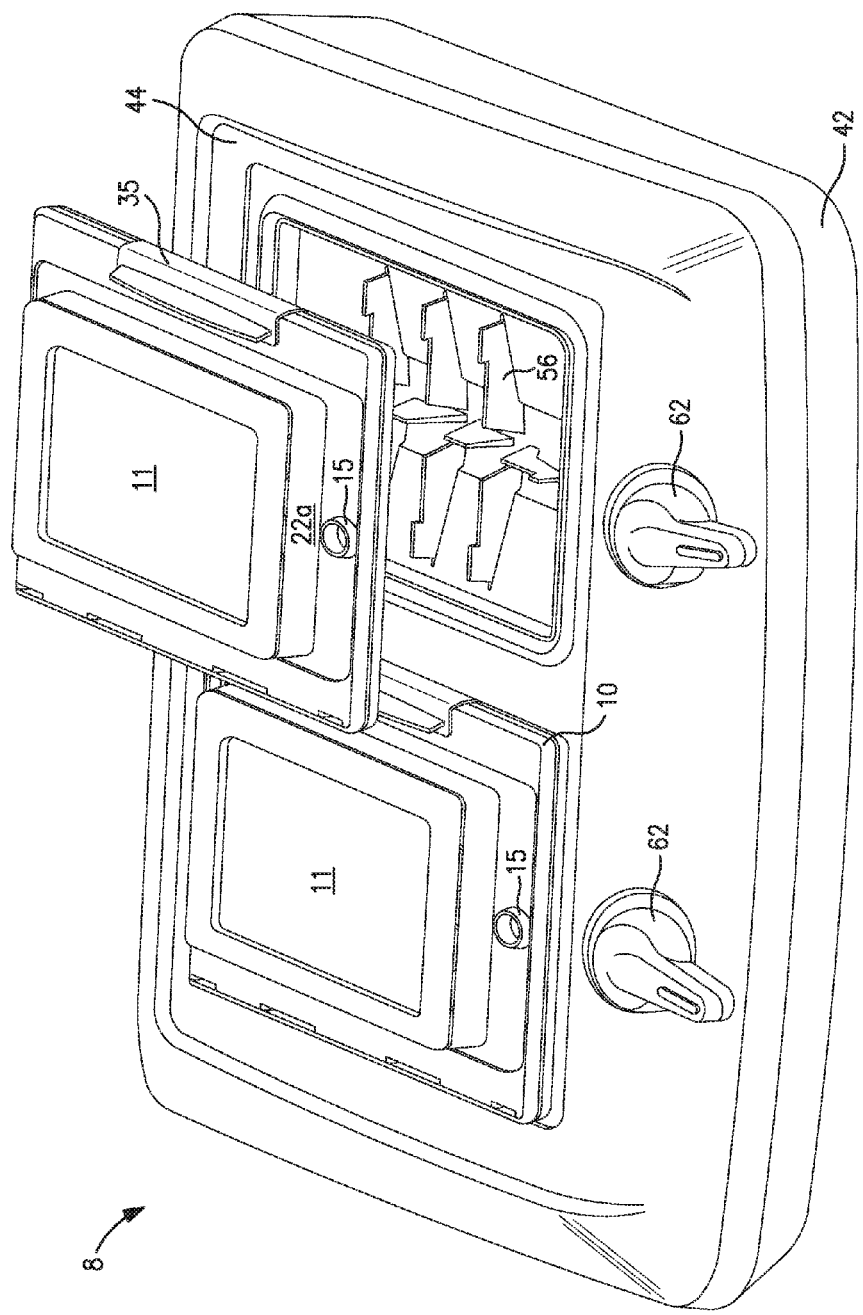
FIG. 10 is an exploded perspective view of a manifold, including carriers, in accordance with certain embodiments.

As shown in FIGS. 9 and 10, in accordance with certain embodiments, manifold 8 is a vacuum manifold that can be attached to a suitable source of vacuum (not shown). The manifold 8 may include a waste collection device (not shown), such as a receptacle, positioned in the manifold (not shown) to collect the liquid pulled through the carrier 10.

In accordance with certain embodiments, the manifold 8 has a base 42, having a drain and support surface 44 on which one or more carriers 10 is placed. The support surface 44 includes one or more wells or carrier receiving regions 55A, 55B (two shown in FIG. 9) that may include a plurality of upstanding ribs 56 that receive the underside of the carrier bottom plate 13 to hold the carrier 10 in a stable manner in the manifold 8. Also shown are optional respective controls 62 for managing and monitoring the manifold 8 and the process. The device can be used with automated liquid handlers and the like if desired. Where the manifold 8 is subdivided into one or more wells or carrier receiving regions, the manifold can process more than one holder to run parallel carriers with different blotting membranes or subparts of one blotting membrane, each membrane is typically processed with at least one different reagent. The manifold 8 can have a common pressure source or each station carrier receiving region can be pressure controlled individually.

In another embodiment, the manifold has leveling feet that when used in conjunction with one or more level indicators of one embodiment of the carrier allow the manifold and carrier to be leveled in a horizontal plane. In one embodiment, the manifold has a series of feet that are capable of being adjusted in a vertical direction so as to level the manifold in relation to the level indicator(s) on the carrier when the carrier is attached to the manifold. In further embodiment, the series of feet have a screw that fits into a threaded portion of the manifold bottom to allow the feet to be individually raised or lowered in a vertical direction.

Various methods may be used in the embodiments disclosed herein. The key factor being that they all rely on a vacuum or positive pressure driven filtration of the liquids to access the large inner surface area of the membrane allowing 3-D interaction of all the molecules throughout the depth rather than only 2-D interaction at the surface as has occurred in the past. Where positive pressure is used, the base could be a closed chamber that could contain the carrier, and the lid 11 would become a pressure manifold to apply pressure to the well 22 of the carrier.

The simplest method is to use the embodiments disclosed herein to conduct one or more of washing cycles. Typically each washing cycle is comprised of one or more washing steps. Generally, 2-5 steps are used per cycle.

Another method is to use the embodiments disclosed herein in which each step in which liquid needs to be moved through the blotting membrane such as after incubation of the antibodies or in the washing steps.

In all of these processes, any driving force suitable to move the liquid(s) through the device and into the manifold can be used. This can vary depending upon the membranes selected for blotting and the manifold used, the desired speed of the filtration and the supply of vacuum or positive pressure available to the researcher.

Generally, the vacuum available may vary between 100 and 760 mm Hg (133 millibars and 1013 millibars). The use of valves, pressure restrictors and the like may also be used to keep the vacuum within the allowed ranges for the membranes used. A preferred vacuum manifold of one embodiment uses of a vacuum of about 100 mm Hg. Other suitable vacuum manifolds include but are not limited to the MULTISCREEN™ and MULTISCREEN™ HTS vacuum manifolds available from Millipore Corporation of Billerica, Mass.

Generally the positive pressure is supplied by an air line at pressures ranging from about 2 psi to about 15 psi. The use of valves, pressure restrictors and the like may also be used to keep the pressure within the allowed ranges for the membranes used. Such pressure systems include but are not limited to Amicon® stirred cell devices available from Millipore Corporation of Billerica, Mass. and positive pressure filtration units available from Caliper Life Sciences of Hopkinton, Mass.

To use a device according to the embodiments disclosed herein, one simply takes a holder, opens it and places the blotting membrane(s) on one of the surfaces such that the lower surface of the blotting membrane is adjacent the porous support and the upper surface of the blotting membrane is adjacent the flow distributor when the device is closed around the membrane(s) so as to have no air bubbles between the blot and the flow distributor. Bubbles between these two surfaces can cause areas of no flow. The blot holder is then placed inside the carrier which is then securely closed with the latch mechanism. The device is placed on or in a manifold having a pressure supply (vacuum or positive pressure). Preferably the blotting membrane(s) has been prewet. The pressure (vacuum or positive pressure) is turned on and a liquid, such as a wash liquid or a reagent, is placed in the well of a carrier. The pressure continues until the liquid has been moved through the device and membrane(s). Then the pressure is turned off.

When more than one blotting membrane is used, they can be arranged in series on top of each other and sufficient liquid containing the same desired reagents can be easily moved through the multiple layers in one process step. Generally when more than one layer is used it is preferred that one use between 2 and 10 layers, preferably between 2 and 5 layers at a time.

The liquid can either be added with the pressure supply being off or the supply being turned on only briefly so as to get the liquid into the membrane(s) and is allowed to incubate (such as may be required with the primary or secondary antibodies). The pressure is then turned on to remove the liquid and/or replace it with another used sequentially. Preferably, during washes, the vacuum is left on and remaining washes are added sequentially.

Figure 9A:
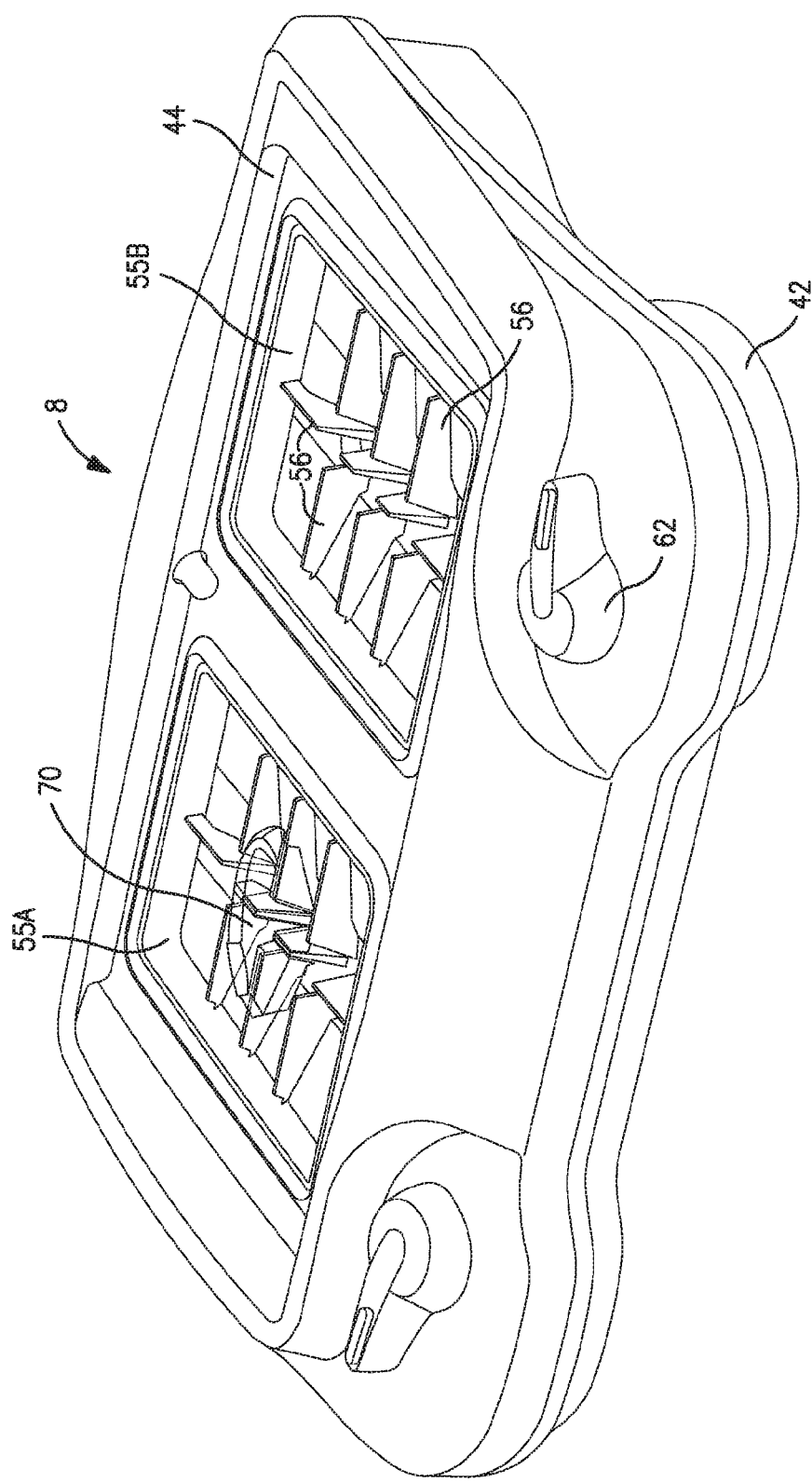
FIG. 9A is a perspective view of a manifold with a collection vessel in accordance with certain embodiments.

Optionally, if one wishes, one can place a collection vessel 70 below the device (FIG. 9A), preferably in the manifold itself or downstream, such as an antibody collection tray. It can then be used to collect one or more unbound reagents that may be expensive and which can be collected and recycled for use in future assays. The vessel can also be subdivided into multiple chambers that are in alignment and fluid communication with the respective portion of the blotting membrane.

Additionally or alternatively, one can place in the downstream flow path below the holder an absorbent matrix that is capable of reversibly binding one or more unbound reagents that are expensive. The matrix is preferably in the form of a monolith, such as a pad, a plug or a paper sheet, that is positioned so that all the liquid passing through the blotting membrane and holder passes through the matrix. It can then either be removed and the reagent eluted or if desired, it can have the bound reagents eluted in situ after completion of the testing of the blotting membrane.

Other processes may also be used with the device of the embodiments disclosed herein.

The membrane contains, in its interstices, one or more substances to be detected. Generally these substances are present in the interstices either by virtue of having been blotted from a solid support for electrophoresis or chromatography or by direct application, usually to detect the presence, absence, or amount of a particular type of material such as an antibody or specific protein—i.e. a Dot-Blot type assay as described above. The definition of the membrane is not limited, however, to these instances, but applies to any case wherein a membrane contains in its interstices one or more substances to be detected. Included in the types of membranes envisioned for use in the embodiments disclosed herein are membranes commonly used to blot electrophoresis gels such as nitrocellulose; nylon; or various other polymeric membranes, such as polyvinylidene fluoride (PVDF), sold as IMMOBILON™ membranes by Millipore Corporation of Billerica, Mass.

A variety of materials can be used to replicate the results of electrophoresis gels performed on various samples as is understood in the art. Most commonly, the samples contain biological substances such as individual proteins, antibodies, nucleic acids, oligonucleotides, complex carbohydrates, and the like, but the application of the technique is not limited to these substances. The technique is applicable to any membrane containing within it a substance to be detected regardless of the chemical composition of the membrane or of the target substances.

When membranes which represent replicas of electrophoretic results are employed, the transfer of the substances to be detected from the gel to the membrane can be conducted by utilizing membranes containing transfer buffer, by electroelution, or by dry blotting of the gels. Techniques for these transfers are well understood in the art, and do not constitute part of the embodiments disclosed herein.

The liquid to be supplied may contain detecting reagents or may simply be provided as a wash. The nature of the detecting reagent depends, of course, on the substance to be detected. Typically, proteins are detected by immunological reactions between antigen and antibody or immunoreactive portions thereof; typically the presence of nucleic acid fragments is detected by suitable oligonucleotide probes. The detecting substances responsible for the immediate or specific reaction with the substance to be detected may be further supplemented, if needed, with label and a multiplicity of applications of the detecting reagents may be needed—e.g., a protocol may include detection of an antigen by supplying an antibody labeled with an enzyme, e.g., commonly, horseradish peroxidase, and then this binding is detected by means of supplying substrate for this enzyme. In application of reagent, it is possible, though not preferred, to use only a positively pressed donor matrix to expose this component of the membrane for a defined period.

It is most convenient to conduct the method of the embodiments disclosed herein at room temperature, but elevated and lower temperatures can also be used. This can be effected by heating the device, its surrounding environment (as in a heat box or cooling box) or the liquids used in the system.

Blots can be sequentially analyzed with multiple antibodies or probes in the present device and process by stripping the previously bound antibodies from the blot followed by subsequent incubations with antibodies or other probes specific other target proteins. The stripping process disrupts the antigen-antibody bonds and dissolves the antibodies in the surrounding buffer. This is usually achieved by a combination of detergent and heat or by exposure to either high or low pH. The device, in combination with the flow distributor, enables the stripping of blots using the high or low pH method. The subsequent reprobing of blots either directly (e.g., using the same flow distributor used for striping) or subsequently after storage, would use the same protocol as the initial probing. Suitable kits for strip blotting are available from Chemicon International, Inc under the brand names of ReBlot™ Plus kit (catalogue #2500), ReBlot Plus-Mild solution (catalogue #2502) and ReBlot Plus-Strong solution (catalogue #2504).

In standard western blotting, the antigen or target is transferred to a membrane support and probed with a suitable probe such as an antibody, protein (e.g., Protein A) or lectin (proteins or glycoproteins which binding to carbohydrate moieties). In some applications, a reverse format (e.g., reverse array) is used, wherein the antibody or other probes are spotted onto a membrane or other support (typically in an array format) and the antigen or target is presented to the immobilized antibodies on the array. Visualization of a target-probe binding event can be achieved by labeling of the antigens or targets or by using a secondary antibody specific for the target. Reverse arrays often employ mixtures of targets, for example lysates labeled with different fluorescent colors to enable parallel processing. Reverse assays can also be performed with the embodiments disclosed herein.

What we claim:

1. A blotting membrane holder for conducting immunoassays, comprising a frame and a porous support, wherein the frame has a perimeter edge configured to support a blotting membrane, and a flow distributor is attached to the frame, and wherein the porous support comprises a polypropylene mesh, and wherein a sheet of paper is laminated to one side of said polypropylene mesh, wherein the polypropylene mesh is bound to the frame along one edge.

2. The blotting membrane holder of claim 1, wherein said frame is made of plastic or paper.

3. The blotting membrane holder of claim 1, wherein said flow distributor is a membrane laminated to said frame.

4. The blotting membrane holder of claim 1, wherein said blotting membrane is sandwiched between said flow distributor and said porous support.

5. The blotting membrane holder of claim 1, wherein more than one blotting membrane is sandwiched between said flow distributor and said porous support.

6. A method of carrying out an immunoassay, comprising:
providing a device comprising a holder and a carrier for the holder, the holder being formed of a material selected from the group consisting of plastic and paper, the holder comprising a frame having a perimeter edge, the frame configured to support a flow distributor; said flow distributor comprising a membrane attached to said frame and over which a blotting membrane can be positioned; a porous support comprising polypropylene mesh bound to said frame along a portion of said perimeter edge; and a sheet of paper laminated to said polypropylene mesh; and a carrier for the holder comprised of a top plate and a bottom plate, each having a width and a length, a top and bottom surface and a thickness between the top and bottom surfaces, an outer edge and at least one opening, the plates being of a length and width greater than the length and width of the holder, the top plate of the carrier having at least one well and an opening substantially equal in width and length to the holder, the bottom surface of the top plate and the top surface of the bottom plate each having one or more seals in alignment with each other when the two plates are adjacent each other and the seals being arranged on each surface at a width and length greater than that of the opening of the top plate, but less than the outer dimensions of the holder, at least one of the plates has a seal formed adjacent the outer edge of the plate and outward of the seal of that plate;
placing a blotting membrane on one of the surfaces of an open holder such that the lower surface of the blotting membrane faces the porous support and the upper surface of the blotting membrane faces the flow distributor when the device is closed around the membrane;
placing the blot holder inside the carrier which is then securely closed;
placing the carrier on or in a manifold;
applying a driving force to said manifold;
placing a liquid in the at least one well of the top plate of the carrier; and
continuing the application of said driving force until the liquid has been moved through the device and blotting membrane.

7. The method of claim 6, further comprising pre-wetting said blotting membrane prior to placing it in the open holder.

8. The method of claim 6, further comprising analyzing blots on said blotting membrane.

9. The method of claim 6, further comprising collecting a portion of said liquid and recycling the same for future use.

10. The method of claim 6, further comprising placing a second blotting membrane in the holder prior to placing the blot holder inside the carrier.

11. The method of claim 6, wherein said driving force is vacuum.

12. The method of claim 6, wherein said driving force is positive pressure.

13. The method of claim 6, wherein said manifold has first and second carrier receiving regions for respectively receiving first and second carriers to carry out two immunoassays in parallel.

* * * * *